US006900354B2

(12) United States Patent
Jolidon et al.

(10) Patent No.: US 6,900,354 B2
(45) Date of Patent: May 31, 2005

(54) 3-PHENYL-PROPIONAMIDO, 3-PHENYL-ACRYLAMIDO AND 3-PHENYL-PROPYNAMIDO DERIVATIVES

(75) Inventors: Synese Jolidon, Blauen (CH); Rosa Maria Rodriguez Sarmiento, Basel (CH); Andrew William Thomas, Birsfelden (CH); Wolfgang Wostl, Grenzach-Wyhlen (DE); Rene Wyler, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 17 days.

(21) Appl. No.: 10/613,785

(22) Filed: Jul. 3, 2003

(65) Prior Publication Data

US 2004/0034096 A1 Feb. 19, 2004

(30) Foreign Application Priority Data

Jul. 15, 2002 (EP) .............................. 02015583

(51) Int. Cl.$^7$ ................ C07C 233/09; C07C 231/02; A61K 31/165
(52) U.S. Cl. ................ 564/161; 564/171; 564/138; 564/134; 514/617
(58) Field of Search ............... 564/134, 138, 564/161, 171; 514/617

(56) References Cited

FOREIGN PATENT DOCUMENTS

| FR | 2645019 | * 10/1990 |
|----|---------|-----------|
| WO | WO 90 11997 | 10/1990 |
| WO | WO 96/40095 | 12/1996 |
| WO | WO 97/33572 | 9/1997 |
| WO | WO 01/34172 | 5/2001 |

OTHER PUBLICATIONS

Benedetti et al., Biochem Pharmacol. vol. 38: No. 4 p. 555–561 (1989).
Saura et al., Neuroscience vol. 70: No. 3, p. 755–774 (1996).
Bentué Ferrer et al., CNS Drugs 6: p. 217–236 (1996).
Gardner et al., J. Clin. Psychiatry vol. 57: No. 3, p. 99–104 (1996).
Greenspan et al. J. Med. Chem. 42: p. 164–172 (1999).
Drechsler et al., Eur. J. Org. Chem. p. 3441–3453 (1999).
Austin et al., J. Org. Chem. 46: p. 2280–2286 (1981).
Eckert et al., Synth. Commun. 28(2), p. 327–335 (1998).
Schlaeger & Christensen, Cytotechnology vol. 30: p. 71–83 (1999).
Zhou & Panchuk–Voloshina, Analytical Biochemistry vol. 253: p. 169–174 (1997).
Jaen, J. et al., J. Med. Chem. 31: p. 1621–1625 (1988).
Rano, Thomas A. et al: "Solid phase synthesis of aryl ethers via the Mitsunobu reaction" Tetrahedron Letters (1995), 36(22), 3789–92.

* cited by examiner

Primary Examiner—Shailendra Kumar
(74) Attorney, Agent, or Firm—George W. Johnston; Patricia S. Rocha-Tramaloni; Kimberly J. Prior

(57) ABSTRACT

The invention relates to 3-phenyl-propionamido, 3-phenyl-acrylamido and 3-phenyl-propynamido derivatives, for example, deriviatives of the formula

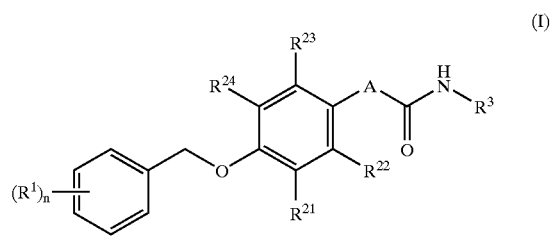

(I)

wherein A is selected from

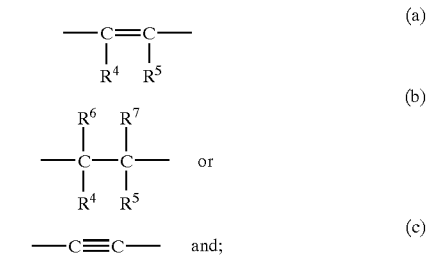

$R^1$, $R^3$, $R^4$, $R^5$, $R^6$, $R^7$, $R^{21}$, $R^{22}$, $R^{23}$, $R^{24}$, and n are as defined herein or pharmaceutically acceptable salts thereof. The invention also relates to processes for preparation of such compounds, compositions containing them, and the use of such derivatives as MAO-B inhibitors. The invention further relates to methods for treating or preventing Alzheimer's disease and senile dementia by administering compounds of the invention.

21 Claims, No Drawings

3-PHENYL-PROPIONAMIDO, 3-PHENYL-ACRYLAMIDO AND 3-PHENYL-PROPYNAMIDO DERIVATIVES

FIELD OF THE INVENTION

The present invention relates to new 3-phenyl-propionamido, 3-phenyl-acrylamido and 3-phenyl-propynamido derivatives, to processes for their preparation, and to pharmaceutical compositions containing them. These compounds are selective monoamine oxidase inhibitors and, therefore, are useful for treating or preventing diseases mediated by monoamine oxidase B, such as Alzheimer's disease and senile dementia.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes [Bach et al., Proc. Natl. Acad. Sci. USA 85:4934–4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171–297 (1992)]. Brain MAO-B activity appears to increase with age. This increase has been attributed to the gliosis associated with aging [Fowler et al., J. Neural. Transm. 49:1–20 (1980)]. Additionally, MAO-B activity is significantly higher in the brains of patients with Alzheimer's disease [Dostert et al., Biochem. Pharmacol. 38:555–561 (1989)] and it has been found to be highly expressed in astrocytes around senile plaques [Saura et al., Neuroscience 70:755–774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentué-Ferrer et al. in CNS Drugs 6:217–236 (1996). Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99–104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The present invention relates to highly selective MAO-B inhibitors. In one instance, the invention relates to 3-phenyl-propionamido, 3-phenyl-acrylamido and 3-phenyl-propynamido derivatives, for example, compounds of formula I

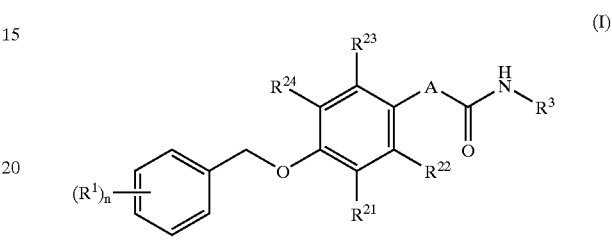

wherein $R^1$, $R^3$, $R^4$, $R^5$, $R^6$, $R^7$, $R^{21}$, $R^{22}$, $R^{23}$, $R^{24}$, A and n are defined herein, or a pharmaceutically acceptable salt thereof. The present invention also relates to compositions containing one or more compounds of the invention and a pharmaceutically acceptable carrier. The invention further relates to a process for the manufacture of compounds of the invention.

Compounds of the present invention are highly selective MAO-B inhibitors. Thus, the present invention also relates to methods for the control or prevention of diseases mediated by monoamine oxidase B. Such diseases include, for example, Alzheimer's disease and senile dementia.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "$(C_1-C_6)$-alkyl" ("lower alkyl") used in the present application denotes straight-chain or branched saturated hydrocarbon residues with 1 to 6 carbon atoms, preferably with 1 to 3 carbon atoms, such as methyl, ethyl, n-propyl, i-propyl, n-butyl, sec-butyl, t-butyl, and the like. Accordingly, the term "$(C_1-C_3)$-alkyl" means a straight-chain or branched saturated hydrocarbon residue with 1 to 3 carbon atoms.

The term "halogen" denotes fluorine, chlorine, bromine and iodine.

"Halogen-$(C_1-C_6)$-alkyl" or "halogen-$(C_1-C_6)$-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. "Halogen-alkoxy" includes trifluoromethyloxy.

"Lower alcohol" or "lower ketone" means a lower alkyl group as defined herein substituted in any position with one or more hydroxy groups or ketone groups, respectively. Examples, of lower alcohols include, but are not limited to, methanol, ethanol, isopropanol, butanol, and the like. Examples of lower ketones include, but are not limited to acetone and butanone.

"$(C_1-C_6)$-Alkoxy" means the residue —O—R, wherein R is a lower alkyl residue as defined herein. Examples of alkoxy radicals include, but are not limited to, methoxy, ethoxy, isopropoxy, and the like.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, compounds of formula I may be converted into pharmaceutically salts. It should be understood that pharmaceutically acceptable salts may be included in the present invention and that all references to pharmaceutically acceptable salts include solvent addition forms (solvates) or crystal forms (polymorphs) of the same acid addition salt.

"Pharmaceutically acceptable," such as pharmaceutically acceptable carrier, excipient, etc., means pharmacologically acceptable and substantially non-toxic to the subject to which the particular compound is administered.

"Therapeutically effective amount" means an amount that is effective to prevent, alleviate, or ameliorate symptoms of disease or prolong the survival of the subject being treated.

The present invention relates to highly selective MAO-B inhibitors, such as 3-phenyl-propionamido, 3-phenyl-acrylamido and 3-phenyl-propynamido derivatives. Compounds of the invention include compounds of formula I

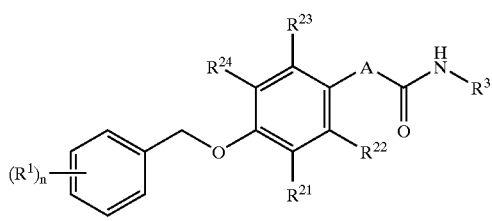

(I)

wherein $R^1$ is $(C_1-C_3)$-alkyl, halogen, halogen-$(C_1-C_6)$-alkyl, cyano, $(C_1-C_6)$-alkoxy or halogen-$(C_1-C_6)$-alkoxy;

$R^{21}$, $R^{22}$, $R^{23}$ and $R^{24}$ are each independently selected from the group consisting of hydrogen and fluoro;

$R^3$ is hydrogen or $(C_1-C_3)$-alkyl;

A is a divalent group of formulae (a), (b) or (c)

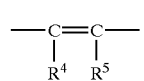

(a)

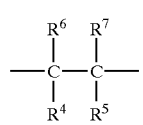

(b)

(c)

$R^4$ is hydrogen or $(C_1-C_3)$-alkyl;

$R^5$, $R^6$ and $R^7$ are each independently hydrogen or $(C_1-C_6)$-alkyl; and n is 1, 2 or 3;

or a pharmaceutically acceptable salt thereof.

Among compounds of the present invention certain compounds of formula I are preferred.

In one embodiment, preferred compounds of formula I are substituted by one, two or three $R^1$ selected from the group consisting of $(C_1-C_3)$-alkyl, halogen, halogen-$(C_1-C_6)$-alkyl, cyano, $(C_1-C_6)$-alkoxy or halogen-$(C_1-C_6)$-alkoxy. Preferably, they are substituted by one $R^1$. Preferred compounds of formula I are those, wherein $R^1$ is halogen or halogen-$(C_1-C_6)$-alkyl. Especially preferred are those compounds of formula I, wherein $R^1$ is fluoro or trifluoromethyl. If two or three groups $R^1$ are present they may be the same or different.

$R^{21}$, $R^{22}$, $R^{23}$ and $R^{24}$ are each independently selected from the group consisting of hydrogen or fluoro. Preferably, $R^{21}$, $R^{22}$, $R^{23}$ and $R^{24}$ are hydrogen.

$R^3$ is hydrogen or $C_1-C_3$-alkyl. Preferably, $R^3$ is hydrogen or methyl; and even more preferably, $R^3$ is methyl.

In another embodiment, preferred compounds are compounds of formula I, wherein A is a divalent group of formula (a), i.e. compounds having the formula I-a

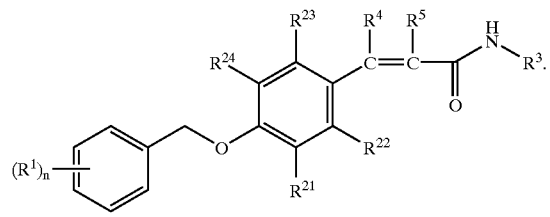

(I-a)

Preferred are compounds of formula I-a are those wherein $R^4$ and $R^5$ are each independently hydrogen or $(C_1-C_3)$-alkyl. All cis- and trans-isomers are included. Especially preferred are compounds of formula I-a wherein $R^3$ is methyl.

A preferred group of compounds within this group of compounds are those, wherein $R^1$ is $(C_1-C_3)$-alkyl or $(C_1-C_6)$-alkoxy.

Examples of such compounds are the following:

N-methyl-3-[4-(4-methyl-benzyloxy)-phenyl]-acrylamide and

3-[4-(3-methoxy-benzyloxy)-phenyl]-N-methyl-acrylamide.

Even more preferred are compounds of formula I-a, wherein $R^4$ and $R^5$ are each independently hydrogen or $(C_1-C_3)$-alkyl, $R^3$ is methyl and $R^1$ is fluoro or trifluoromethyl.

The following are examples of such compounds:

3-[4-(3-fluoro-benzyloxy)-phenyl]-2,N-dimethyl-acrylamide,

3-[4-(3-fluoro-benzyloxy)-phenyl]-N-methyl-acrylamide,

N-methyl-3-[4-(4-trifluoromethyl-benzyloxy)-phenyl]-acrylamide,

3-[4-(3,4-difluoro-benzyloxy)-phenyl]-N-methyl-acrylamide, and

3-[4-(4-fluoro-benzyloxy)-phenyl]-N-methyl-acrylamide.

In another embodiment, preferred compounds are compounds of formula I, wherein A is a divalent group of formula (b) and $R^4$, $R^5$, $R^6$ and $R^7$ are each independently hydrogen or $(C_1-C_3)$-alkyl, i.e. compounds having the formula I-b

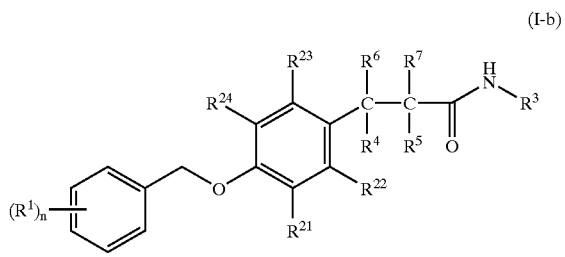

(I-b)

Examples of such compounds are the following:
3-[4-(3-fluoro-benzyloxy)-phenyl]-2,N-dimethyl-propionamide,
3-[4-(3,4-difluoro-benzyloxy)-phenyl]-propionamide, and
3-[4-(3-fluoro-benzyloxy)-phenyl]-N-methyl-butyramide.

Further preferred are compounds of formula I, wherein A is a divalent group of formula (c), i.e. compounds of formula I having the formula I-c

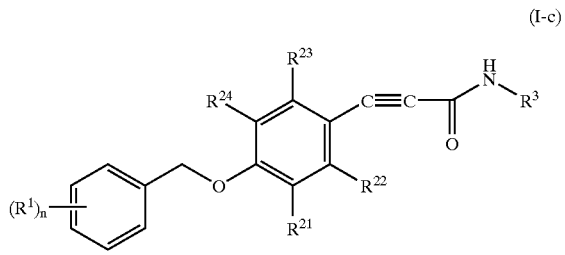

(I-c)

The compound 3-[4-(3-Fluoro-benzyloxy)-phenyl]-propynoic acid methylamide is an example of such a compound.

The compounds of general formula I can be manufactured by reacting a compound of formula II

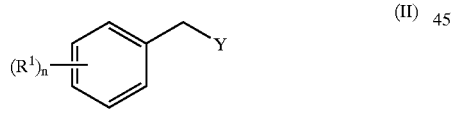

(II)

wherein $R^1$ and n have the above meanings and Y is a leaving group, with a compound of formula III

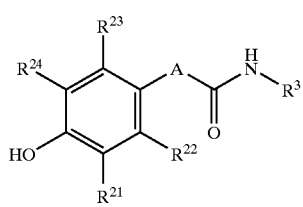

(III)

wherein $R^3$, $R^{21}$, $R^{22}$, $R^{23}$, $R^{24}$ and A have the above meanings,
or, alternatively,
reacting a compound of formula IV

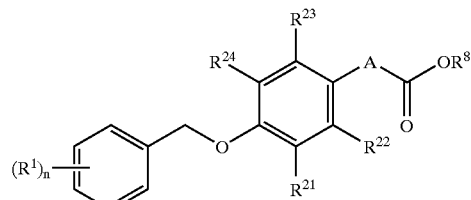

(IV)

wherein $R^1$, $R^{21}$, $R^{22}$, $R^{23}$, $R^{24}$ and n have the above meanings and $R^8$ is hydrogen or $(C_1-C_6)$-alkyl,
with an amine of formula V
$H_2NR^3$ (V)
wherein $R^3$ is as defined above,
to obtain a compound of formula I.

In accordance with the present invention, one method for preparing compounds of general formula I is shown in scheme 1:

Scheme 1

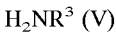

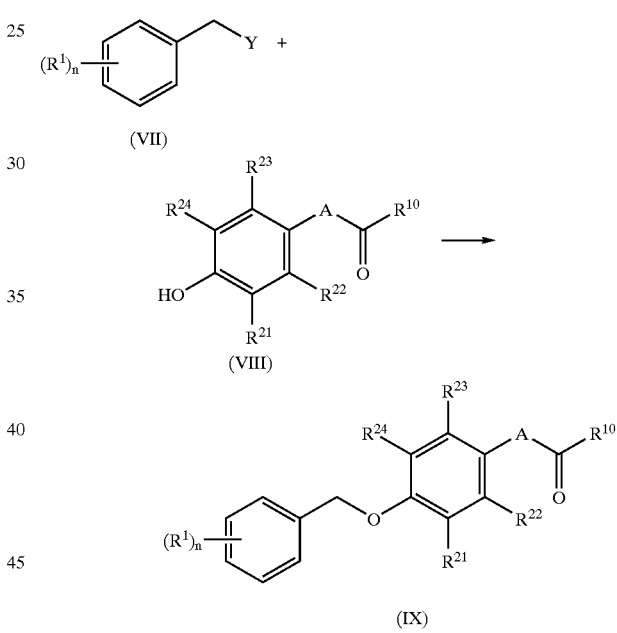

wherein Y is a leaving group (halogen, OTf etc.) or OH (for Mitsunobu-coupling), $R^{10}$ is OAlkyl or $NHR_3$ and $R^1$, $R^{10}$, $R^{21}$, $R^{22}$, $R^{23}$, $R^{24}$, A and n are as defined above.

Ethers of the type IX are formed by Williamson-ether synthesis, starting from the corresponding p-substituted phenols VIII and benzylic halides, tosylates, mesylates or triflates VII. Bases used can be for example alcoholates or carbonates (sodium, potassium or cesium carbonate). Preferred solvents are lower alcohols, acetonitrile or lower ketones at temperatures between 20° C. and reflux temperature. Another approach is the Mitsunobu-coupling of benzylic alcohols with the corresponding phenols VIII. The reaction is done as usual in inert solvents like for example diethyl ether or tetrahydrofurane (THF), using dialkyl-azo-dicarboxylates in presence of phosphines (for example tributyl- or triphenyl-phosphine). When $R^{10}$ is $NHR^3$, these reactions lead directly to the desired compounds of formula I. If $R^{10}$ is OAlkyl, the ester of formula IX can be transformed into the desired final product of general formula I using standard procedures: aminolysis with $R^3NH_2$ in solvents like methanol, THF etc., or saponification to the acid (for example KOH in methanol), activation of the acid via acid chloride (thionyl chloride or oxalyl chloride) or activation with N,N'-Dicyclohexylcarbodiimide (DCC), N-(3-dimethylamino-propyl)-N'-ethyl-carbodiimide hydrochloride (EDC) etc. and coupling with the amine $R^3NH_2$.

Another method (Scheme 2) to prepare compounds of formula I where A is a divalent group of formula (a) —$CR^4$=$CR^5$— involves Knoevenagel-Doebner condensations of the ketones or aldehydes X with malonates or dialkyl malonates XI. These reactions are done under standard conditions, using pyridine as a solvent, with or without piperidine catalysis, preferentially at reflux temperature.

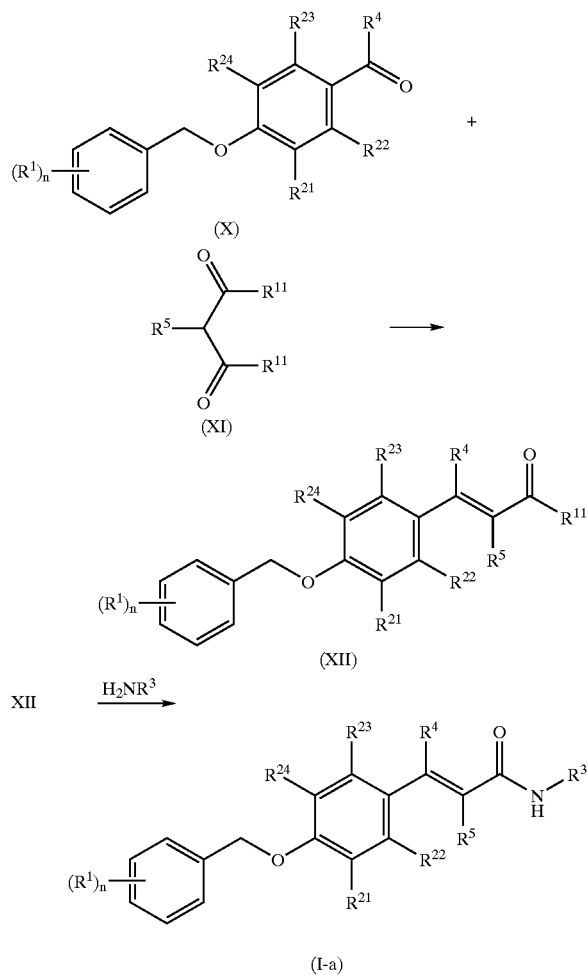

wherein $R^{11}$ is Oalkyl or OH and $R^1$, $R^4$, $R^5$, $R^{21}$, $R^{22}$, $R^{23}$, $R^{24}$ and n have the meanings as defined above.

The esters XII ($R^{11}$=OAlkyl) or acids XII ($R^{11}$=OH) are then converted as previously described to the desired amides of formula I-a. Alternatively, the compounds XII can be reduced to the derivatives I-b wherein A=—$CHR^4$—$CHR^5$—, before or after conversion to the amides (scheme 3). This reduction is preferentially done by catalytic hydrogenation using hydrogen and platinum on charcoal in solvents like methanol, dioxane or ethyl acetate at RT.

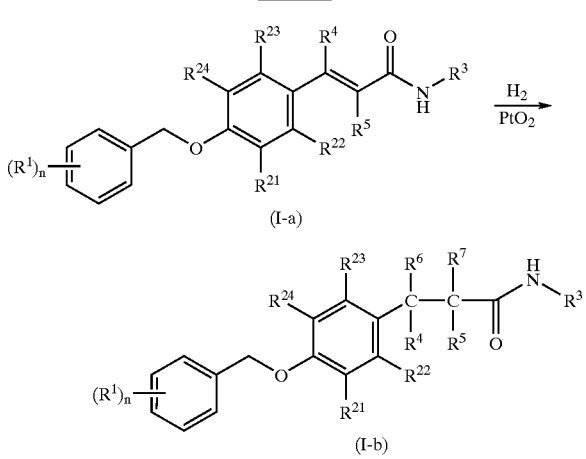

The compounds X can be prepared by alkylation of optionally substituted 4-hydroxy-benzaldehydes or 4-hydroxy-acetophenones with benzylic halides, tosylates, mesylates or triflates in a reaction similar to the one depicted in scheme 1.

Compounds of formula I wherein A is —$CR^4$=$CR^5$— can also be prepared by a Reformatsky-reaction on compounds X (scheme 4).

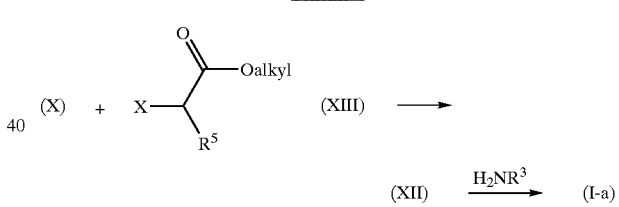

wherein X is halogen and $R^5$ has the meanings as defined above.

These condensations of the carbonyl compounds with the alpha-halo-esters are done under standard conditions in ethers like diethyl ether, THF or dioxane with preferentially zinc as a metal. Compounds XII can be further converted as previously described to the desired amides of formula I-a.

Another method (scheme 5) to prepare compounds of the type I-a or I-c involves Heck- or Sonogashira-couplings of aryl halides or triflates XIV with alkenes, respectively alkynes.

Compounds XIV can be prepared by reacting 4-halo-phenols with benzylic halides or triflates VII or by Mitsunobu-coupling with benzylic alcohols in a manner similar to scheme 1.

Scheme 5

Heck reaction

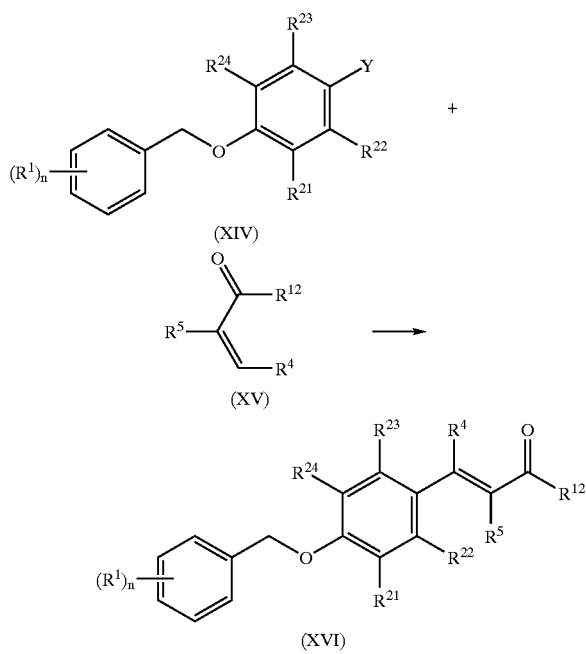

Sonogashira reaction

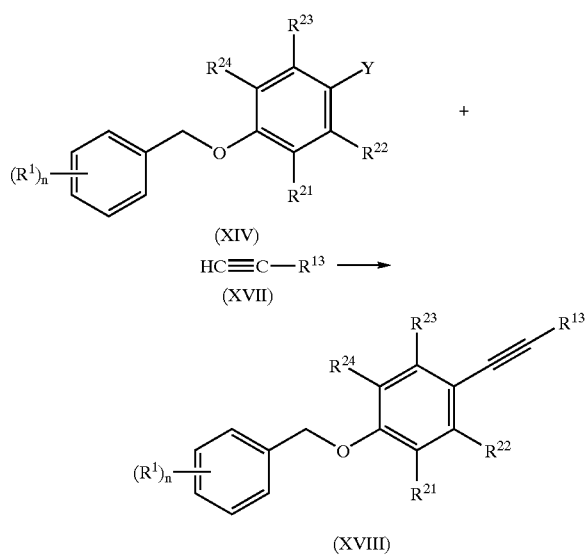

wherein $R^{12}$ is Oalkyl or $NHR_3$ and $R^{13}$ is H, Si(alkyl)$_3$, COOalkyl or CONHR$^3$ and $R^1$, $R^4$, $R^5$, $R^{21}$, $R^{22}$, $R^{23}$, $R^{24}$, n and Y have the meanings as defined above.

Heck-reactions were performed using standard procedures [see Greenspan et al., J. Med. Chem. 42:164 (1999) or Hanack et al., Eur. J. Org. Chem. 3441 (1999)].

Compounds XV are commercially available alpha-beta unsaturated esters or amides.

Sonogashira-couplings can be done using palladium catalysis under standard conditions [Lau et al., J. Org. Chem. 46:2280 (1981) or Ipaktschi et al., Synth. Commun. 28:327 (1998)].

Compounds XVII are commercially available alkynes.

Compounds of the type XVI, wherein $R^{12}$ is OAlkyl, are converted to the amides I-a (A=—CR$^3$=CR$^4$—) by the procedures described earlier. Compounds of the type XVIII, wherein $R^{13}$ is —Si(Alkyl)$_3$ XIX, are converted to the amides I-c (A=—C≡C—) by standard procedures, as described for example in scheme 6.

Scheme 6

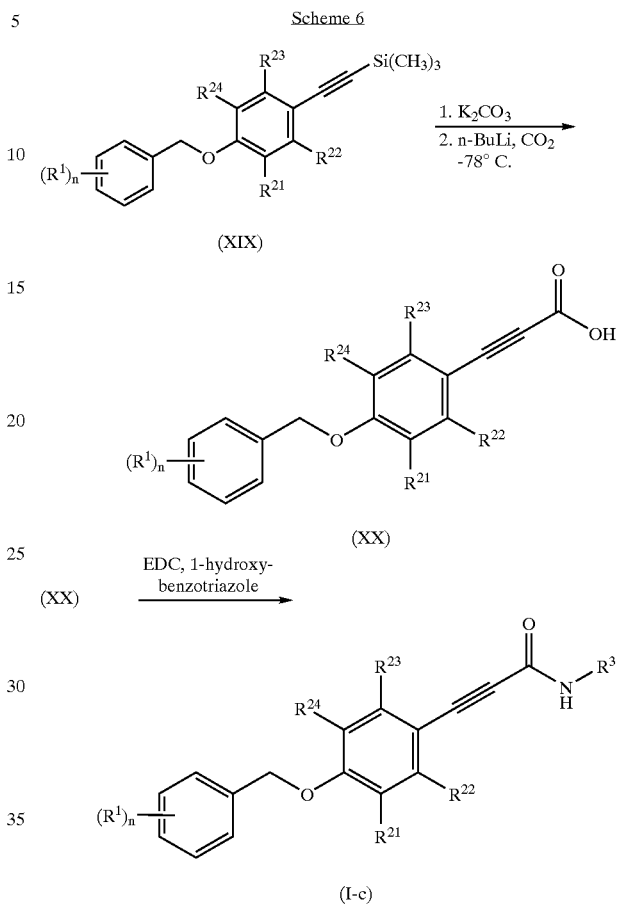

Compounds XX are prepared by first deprotecting compounds XIX with sodium or potassium carbonate in methanol, then deprotecting the alkyne with strong bases like n-BuLi or LDA, and quenching the anion with carbon dioxide. The acids XX are then converted to the amides I-c by activation with DCC, EDC or CDI, followed by the addition of the corresponding amine $R^3$—NH$_2$.

The compounds of the invention are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (WO 01/34,172), peripheral neuropathy caused by cancer chemotherapy (WO 97/33,572), or the treatment of multiple sclerosis (WO 96/40,095) and other neuroinflammatory diseases.

The compounds of the invention are especially useful for the treatment and prevention of Alzheimer's disease and senile dementia.

The pharmacological activity of the compounds was tested using the following method. The cDNAs encoding human MAO-A and MAO-B were transiently transfected into EBNA cells using the procedure described by Schlaeger and Christensen [Transient Gene Expression in Mammalian Cells Grown in Serum-free Suspension Culture; Cytotechnology, 15:1–13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [A One-Step Fluorometric Method for the Continuous Measurement of Monoamine Oxidase Activity, Analytical Biochemistry 253:169–174 (1997)]. Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horse-radish peroxidase (Roche Biochemicals) and 80 $\mu$M N-acetyl-3,7,-dihydroxyphenoxazine (Amplex Red, Molecular Probes). The samples were further incubated for 30 min at 37° C. in a final volume of 200 $\mu$l and absorbance was then determined at a wavelength of 570 nm using a SpectraMax plate reader (Molecular Devices). Background (non-specific) absorbance was determined in the presence of 10 $\mu$M clorgyline for MAO-A or 10 $\mu$M L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of preferred compounds of formula I as measured in the assay described above are in the range of 1 $\mu$M or less, typically 0.1 $\mu$M or less, and ideally 0.02 $\mu$M or less.

In the table below some specific $IC_{50}$ values of preferred compounds are described:

| Compound | MAO-B $IC_{50}$ ($\mu$mol) | MAO-A $IC_{50}$ ($\mu$mol) |
| --- | --- | --- |
| 3-[4-(3-fluoro-benzyloxy)-phenyl]-2-methyl-acrylamide | 0.083 | >10000 |
| 3-[4-(3-fluoro-benzyloxy)-phenyl]-2,N-dimethyl-propionamide | 0.029 | >10000 |
| 3-[4-(3-fluoro-benzyloxy)-phenyl]-propynoic acid amide | 0.098 | 5620 |

The present invention also provides pharmaceutical compositions containing compounds of the invention, or pharmaceutically acceptable salts thereof, and a pharmaceutically acceptable carrier. Such pharmaceutical compositions can be in the form of tablets, coated tablets, dragées, hard and soft gelatine capsules, solutions, emulsions or suspensions. The pharmaceutical compositions can also be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the present invention are selective MAO-B inhibitors. Therefore, the present invention also provides methods of treating or preventing diseases that are mediated by monoamine oxidase B. Such methods include administering a therapeutically effective amount of a compound of the invention, for example, a compound of formula I, or a pharmaceutically acceptable salt thereof, to an individual in need of such treatment. In one embodiment, the invention provides a method for the treatment or prevention of Alzheimer's disease by administering to an individual a therapeutically effective amount of a compound of formula I, for example, a compound of formula I-a, I-b, or I-c. In another embodiment, the present invention provides a method for the treatment or prevention of senile dementia by administering to an individual a therapeutically effective amount of a compound of formula I, for example, a compound of formula I-a, I-b, or I-c.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories or parenterally, for example, in the form of injection solutions.

The dosage at which the compound of the invention is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. The following abbreviations are used: RT: room temperature; THF: tetrahydrofurane. Unless otherwise, indicated, the following examples have been performed regardless of the tense in which they are written.

EXAMPLE 1

3-[4-(3-Fluoro-benzyloxy)-phenyl]-2-methyl-acrylamide a) 1-(3-Fluorobenzyloxy)-4-iodo-benzene A solution of 3.0 g (15.9 mmol) of 4-iodophenol and 3.49 g (15.9 mmol) of 3-fluorobenzyl bromide in 30 ml ethanol is treated dropwise at RT with 20 ml of a 1 molar solution of sodium ethanolate in ethanol. The reaction mixture is refluxed for 4 h and the precipitated sodium bromide is filtered off. The filtrate is evaporated to dryness, treated with 100 ml of water, acidified by addition of citric acid and extracted three times with dichloromethane. After drying and evaporation, the residue is subjected to chromatography on silica gel (hexane/ethyl acetate 9:1). This yields 4.23 g (81%) of a colorless solid. mp=48° C.

b) 3-[4-(3-Fluoro-benzyloxy)-phenyl]-2-methyl-acrylic acid methyl ester

A mixture of 1.2 g (3.7 mmol) of 1-(3-fluorobenzyloxy)-4-iodo-benzene, 2.06 g (14.9 mmol) of potassium carbonate and 1.70 g (52.8 mmol) of tetrabutyl ammonium bromide in 10 ml of dimethylformamide is treated under Ar with 48 mg (0.21 mmol) of palladium-(II)-acetate. 1.49 g (14.9 mmol) of methyl methacrylate is added and the mixture heated at 90° C. for about 40 min. The reaction mixture is poured into 150 ml dichloromethane, filtered and washed successively with 0.1 molar hydrochloric acid, saturated aqueous sodium hydrogencarbonate and water. The solution is dried over magnesium sulfate. Flash chromatography (silica gel, hexane/ethyl acetate 95:5) yields 461 mg (42%) of a colorless solid. MS: m/e=301.3 (M$^+$+H).

c) 3-[4-(3-Fluoro-benzyloxy)-phenyl]-2-methyl-acrylic acid 383 mg (1.28 mmol) of 3-[4-(3-fluoro-benzyloxy)-phenyl]-2-methyl-acrylic acid methyl ester is added to a solution of 143 mg (2.55 mmol) potassium hydroxide in 7 ml methanol. The solution is stirred at 65° C. for about 3 h, evaporated to dryness, treated with aqueous 0.1 molar hydrochloric acid and extracted 3 times with ethyl acetate. Evaporation of the solvent leaves the pure acid. 305 mg (84%) of a colorless solid. MS (neg.ions): m/e=285.0 (M−H).

d) 3-[4-(3-Fluoro-benzyloxy)-phenyl]-2-methyl-acrylamide 305 mg (1.07 mmol) of 3-[4-(3-fluoro-benzyloxy)-phenyl]-2-methyl-acrylic acid is dissolved in 8 ml of dichloromethane and one drop of dimethylformamide is added. The solution is cooled to 0° C. and treated dropwise with 676 mg (5.33 mmol) oxalyl chloride. The resulting solution is stirred at 0° C. for additional 30 minutes, then 2 hours at RT. Evaporation of the solvent leaves the crude acid chloride which is dissolved in 5 ml THF. This solution is slowly added under stirring to 10 ml of concentrated ammonia. The precipitate is filtered off and recrystallised from methanol to yield 199 mg (65%) of a colorless solid. MS: m/e=286.2 (M$^+$+H).

EXAMPLE 2

3-[4-(3-Fluoro-benzyloxy)-phenyl]-2,N-dimethyl-acrylamide

The title compound is prepared in analogy to example 1 d), using aqueous methylamine instead of ammonia. Yield=99%. Slightly yellow solid. MS: m/e=300.2 (M$^+$+H).

EXAMPLE 3

3-[4-(3-Fluoro-benzyloxy)-phenyl]-2-methyl-propionamide

A solution of 50 mg of 3-[4-(3-fluoro-benzyloxy)-phenyl]-2-methyl-acrylamide in 10 ml methanol is treated with 4 mg of platinum dioxide and hydrogenated at RT and normal pressure for about 4 h. The catalyst is filtered off and the filtrate evaporated to dryness. Trituration of the residue in about 2 ml diethylether yields 12 mg (23%) of a colorless solid. MS: m/e=288.2 (M$^+$+H).

EXAMPLE 4

3-[4-(3-Fluoro-benzyloxy)-phenyl]-2,N-dimethyl-propionamide

The title compound is prepared in analogy to example 3, starting from 3-[4-(3-fluoro-benzyloxy)-phenyl]-2,N-dimethyl-acrylamide. Yield=52% of a colorless solid. MS: m/e=302.3 (M$^+$+H).

EXAMPLE 5

3-[4-(3-Fluoro-benzyloxy)-phenyl]-propynoic acid amide a) [4-(3-Fluoro-benzyloxy)-phenylethynyl]-trimethyl-silane A well stirred suspension of 4.0 g (12.2 mmol) of 1-(3-fluorobenzyloxy)-4-iodo-benzene, 0.23 g (1.22 mmol) of cuprous iodide and 0.856 mg (1.22 mmol) of dichloro bis(triphenylphosphine) palladium(II) in a mixture of 20 ml THF and 10 ml triethylamine is treated dropwise with 1.44 g (14.6 mmol) of trimethylsilyl acetylene. The reaction is exothermic. The mixture is stirred overnight at RT, treated with saturated aqueous ammonium chloride and extracted three times with ethyl acetate. The organic phase is dried, concentrated and subjected to flash-chromatography (silica gel, cyclohexane) to yield 3.48 g (95%) of a slightly orange oil. NMR (CDCl$_3$; 300 MHz): 0.24 ppm (s, 9H); 5.06 ppm (s, 2H); 6.85–7.45 ppm (m, 8H).

b) 1-(3-Fluoro-benzyloxy)-4-ethynyl-benzene

A solution of 2.06 g (6.9 mmol) of [4-(3-fluoro-benzyloxy)-phenylethynyl]-trimethyl-silane in 35 ml methanol is treated with 95 mg (0.69 mmol) of solid potassium carbonate. The mixture is stirred at RT for 3 h, concentrated and treated with saturated aqueous sodium hydrogencarbonate. The compound is extracted three times with dichloromethane, dried over magnesium sulfate and concentrated to yield 1.53 g (98%) of a slightly brown oil. MS (neg.ions): m/e=225.4 (M−H).

c) [4-(3-Fluoro-benzyloxy)-phenyl]-propynoic acid 1.93 g (8.5 mmol) of 1-(3-fluoro-benzyloxy)-4-ethynyl-benzene is dissolved in 30 ml THF and cooled to −78° C. 5.8 ml (9.4 mmol) of a 1.6 molar solution of n-butyl lithium is slowly added under stirring. The resulting solution is stirred at −78° C. for 30 minutes. An excess of solid carbon dioxide is added and the suspension is slowly allowed to warm to RT. Water is added and the mixture is acidified by addition of aqueous 0.1 molar hydrochloric acid. Extraction with ethyl acetate yields a semi-solid residue which is triturated in diethyl ether to give 1.58 g (68%) of a colorless solid. MS (neg.ions): m/e=269.1 (M−H).

d) 3-[4-(3-Fluoro-benzyloxy)-phenyl]-propynoic acid amide 50 mg (0.19 mmol) of [4-(3-fluoro-benzyloxy)-phenyl]-propynoic acid is dissolved in 3 ml of THF and treated with 27 mg (0.2 mmol) of 1-hydroxybenzotriazole and 37 mg (0.19 mmol) of N-(3-dimethylaminopropyl)-N'-ethyl-carbodiimide hydrochloride. The resulting mixture is stirred at RT for 30 minutes, cooled to 0° C. and treated with 1 ml of concentrated ammonia. The suspension is stirred overnight at RT, diluted with water and extracted three times with dichloromethane. Flash-chromatography (silica gel, dichloromethane/methanol) yields 29 mg (59%) of a colorless solid. MS: m/e=270.2 (M$^+$+H).

EXAMPLE 6

3-[4-(3-Fluoro-benzyloxy)-phenyl]-propynoic acid methylamide

The title compound is prepared in analogy to example 5 d), starting from [4-(3-fluoro-benzyloxy)-phenyl]-propynoic acid and aqueous methylamine. Colorless solid. Yield=45%. MS: m/e=284.1 (M$^+$+H).

EXAMPLE 7

3-[4-(3,4-Difluoro-benzyloxy)-phenyl]-propionamide

A mixture of 106 mg (0.64 mmol) 3-(4-hydroxy-phenyl)-propionamide, 178 mg (1.29 mmol) potassium carbonate and 140 mg (0.68 mmol) 3,4-difluorobenzyl bromide in 5 ml ethyl methyl ketone is hold at 50° C. for 24 hours. The reaction mixture is cooled, diluted with water and extracted with diethyl ether. Crystallization from n-hexane yields 77 mg (41%) of a colorless solid. MS: m/e=291.3 (M$^+$).

EXAMPLE 8

3-[4-(3-Fluoro-benzyloxy)-phenyl]-N-methyl-acrylamide a) 3-[4-(3-Fluoro-benzyloxy)-phenyl]-acrylic acid 3-fluoro-benzyl ester A mixture of 5.0 g (30.5 mmol) p-cumaric acid, 8.4 g (61 mmol) potassium carbonate and 11.5 g (61 mmol) 3-fluorobenzylbromide in 500 ml ethyl methyl ketone is hold over night at 80° C. The reaction mixture is cooled, diluted with water and extracted with ethyl acetate. Chromatography (silica gel, n-hexane/ethyl acetate 4:1) gives 6.48 g (56%) of a colorless solid. MS: m/e=380.2 (M$^+$).
b) 3-[4-(3-Fluoro-benzyloxy)-phenyl]-acrylic acid 6.48 g (17 mmol) 3-[4-(3-fluoro-benzyloxy)-phenyl]-acrylic acid 3-fluoro-benzyl ester is dissolved in 100 ml THF and 1.36 g (34 mmol) solid sodium hydroxide is added. The reaction mixture is heated overnight at 50° C., cooled and acidified with 1N hydrochloric acid. The precipitate is filtered off and washed with cold water to give 4.43 g (96%) of a colorless solid. MS: m/e=271.2 (M–H).
c) 3-[4-(3-Fluoro-benzyloxy)-phenyl]-acryloyl chloride 3.0 g (11 mmol) 3-[4-(3-fluoro-benzyloxy)-phenyl]-acrylic acid is suspended in 50 ml dichloromethane and 4.0 ml (55 mmol) of thionyl chloride is added. The reaction mixture is hold at RT for 1 hour, then heated to 50° C. overnight. Evaporation yields 3.56 g (111%) of the crude acid chloride as a yellowish solid. MS: m/e=290.2 (M$^+$).
d) 3-[4-(3-Fluoro-benzyloxy)-phenyl]-N-methyl-acrylamide 500 mg (1.72 mmol) of the crude 3-[4-(3-fluoro-benzyloxy)-phenyl]-acryloyl chloride is dissolved in 2 ml dichloromethane and 0.4 ml of a 41% solution of methylamine in water is added. The reaction mixture is heated under reflux for about 3 hours, cooled, filtered and washed with cold dichloromethane to yield 149 mg (30%) of a colorless solid. MS: m/e=286.2 (M$^+$).

EXAMPLE 9

3-[4-(3-Fluoro-benzyloxy)-phenyl]-acrylamide 500 mg (1.72 mmol) of the crude 3-[4-(3-fluoro-benzyloxy)-phenyl]-acryloyl chloride as prepared in Example 8c) is dissolved in 2 ml dichloromethane and 4 ml of concentrated ammonia is added. The mixture is hold at reflux temperature for about 4 hours, cooled and filtered. The solid is subjected to column chromatography (silica gel, dichloromethane/methanol/ammonia 140:10:1) to give 89 mg (19%) of a colorless solid. MS: m/e=272.2 (M$^+$+H).

EXAMPLE 10

N-Ethyl-3-[4-(3-fluoro-benzyloxy)-phenyl]-acrylamide

The title compound is prepared in analogy to example 9, using crude 3-[4-(3-fluoro-benzyloxy)-phenyl]-acryloyl chloride and a 2 M solution of ethylamine in dichloromethane. Colorless solid. Yield=72%. MS: m/e=300.3 (M$^+$+H).

EXAMPLE 11

N-Methyl-3-[4-(4-trifluoromethyl-benzyloxy)-phenyl]-acrylamide a) 3-(4-Hydroxy-phenyl)-N-methyl-acrylamide 6.0 g (36.5 mmol) p-cumaric acid is dissolved in 10 ml dichloromethane. 3 drops of N,N-dimethylformamide is added, followed by 10 ml of thionyl chloride. The mixture is stirred at RT for 15 min, concentrated and treated with 5 ml of a 41% solution of methylamine in water. After stirring at RT for about 2 hours, the methylamine is stripped off and the residue treated with water, extracted with dichloromethane and subjected to column chromatography (silica gel, dichloromethane/methanol/ammonia 140:10:1), yielding 670 mg (10%) of a colorless solid. MS: m/e=177 (M$^+$).
b) N-Methyl-3-[4-(4-trifluoromethyl-benzyloxy)-phenyl]-acrylamide 195 mg (1.1 mmol) 3-(4-hydroxy-phenyl)-N-methyl-acrylamide is dissolved in 25 ml ethyl methyl ketone and 304 mg (2.2 mmol) potassium carbonate is added, followed by 289 mg (1.2 mmol) of 4-(trifluoromethyl)benzyl bromide. The reaction mixture is stirred overnight at RT, heated to 50° C. for 3 hours, treated with water and extracted 3 times with dichloromethane. The extract is dried over magnesium sulfate, concentrated and treated with ether to yield 260 mg (70%) of a colorless solid. MS: m/e=336.1 (M$^+$+H).

EXAMPLE 12

3-[4-(3,4-Difluoro-benzyloxy)-phenyl]-N-methyl-acrylamide a) 3-[4-(3,4-Difluoro-benzyloxy)-phenyl]-acrylic acid 2.5 g (15.2 mmol) p-cumaric acid is dissolved 100 ml ethyl methyl ketone. 4.21 g (30.5 mmol) potassium carbonate and 6.31 g (30.5 mmol) 3,4-difluorobenzyl bromide are added and the reaction mixture is hold at 70° C. over night. Dilution with water and extraction with ethyl acetate leaves a solid which is recrystallised from diethyl ether/n-hexane. The crude ester so obtained is dissolved in 100 ml THF and treated with 30.5 ml (30.5 mmol) of an aqueous 1 N sodium hydroxide solution. The mixture is heated to 50° C. for 6 hours, cooled and acidified with 1 N hydrochloric acid. The precipitate is filtered off and dried to yield 3.24 g (73%) of a colorless solid. MS: m/e=288.9 (M–H).
b) 3-[4-(3,4-Difluoro-benzyloxy)-phenyl]-N-methyl-acrylamide 500 mg (1.72 mmol) 3-[4-(3,4-difluoro-benzyloxy)-phenyl]-acrylic acid is suspended in 5 ml dichloromethane. 0.62 ml (8.6 mmol) thionyl chloride is added and the reaction mixture heated overnight to 45° C. Concentration leaves a yellowish tar which is dissolved again in 10 ml dichloromethane and treated with 1.1 ml of a 33% solution of methylamine in ethanol. After heating at 45° C. for 3 hours, the reaction mixture is filtered and the filtrate concentrated. Chromatography (silica gel, dichloromethane/methanol) yields 136 mg (26%) of a colorless solid. MS: m/e=304.1 (M$^+$+H).

EXAMPLE 13

3-[4-(4-Fluoro-benzyloxy)-phenyl]-N-methyl-acrylamide a) 3-[4-(4-Fluoro-benzyloxy)-phenyl]-acrylic acid The title compound is prepared in analogy to example 12 a) from p-cumaric acid and 4-fluorobenzyl bromide. Yield=56%. Colorless solid. MS: m/e=271.0 (M–H).

b) 3-[4-(4-Fluoro-benzyloxy)-phenyl]-N-methyl-acrylamide

The title compound is prepared in analogy to example 12 b) from 3-[4-(4-fluoro-benzyloxy)-phenyl]-acrylic acid and methylamine. Yield=21%. Colorless solid. MS: m/e=286.0 ($M^++H$).

EXAMPLE 14

3-[4-(3-Cyano-benzyloxy)-phenyl]-N-methyl-acrylamide

The title compound is prepared in analogy to example 11 b) from 3-(4-hydroxy-phenyl)-N-methyl-acrylamide and 3-bromomethyl-benzonitrile. Yield=75%. Colorless solid. MS: m/e=293.2 ($M^++H$).

EXAMPLE 15

N-Methyl-3-[4-(4-methyl-benzyloxy)-phenyl]-acrylamide

The title compound is prepared in analogy to example 11 b) from 3-(4-hydroxy-phenyl)-N-methyl-acrylamide and 1-bromomethyl-4-methyl-benzene. Yield=44%.

Colorless solid. MS: m/e=282.0 ($M^++H$).

EXAMPLE 16

3-[4-(3-Methoxy-benzyloxy)-phenyl]-N-methyl-acrylamide

The title compound is prepared in analogy to example 11 b) from 3-(4-hydroxy-phenyl)-N-methyl-acrylamide and 1-bromomethyl-3-methoxy-benzene. Yield=60%. Colorless solid. MS: m/e=298.2 ($M^++H$).

EXAMPLE 17

3-[4-(3-Fluoro-benzyloxy)-phenyl]-but-2-enoic acid methylamide a) 1-[4-(3-Fluoro-benzyloxy)-phenyl]-ethanone A mixture of 7.5 g (55.1 mmol) 4-hydroxy-acetophenone, 10.93 g (57.8 mmol) 3-fluoro-benzylbromide and 19.74 g (60.6 mmol) cesium carbonate in 75 ml acetonitrile is stirred for 1 hour at RT, then hold 3 hours at reflux temperature. The reaction mixture is concentrated and treated with about 200 ml of ice-water. Extraction with ethyl acetate yields 12.82 g (95%) of a slightly yellowish solid. MS: m/e=245.3 ($M^++H$).

b) 3-[4-(3-Fluoro-benzyloxy)-phenyl]-but-2-enoic acid methyl ester 6.72 g (40 mmol) of trimethylphosphonoacetate is added to 40 ml of a 1M solution of sodium methanolate in methanol. The mixture is stirred for 15 minutes at RT. A solution of 4.89 g (20 mmol) of 1-[4-(3-fluoro-benzyloxy)-phenyl]-ethanone in 40 ml methanol is slowly added at RT. The resulting mixture is refluxed for 20 hours and concentrated, leaving 4.98 g of a yellowish solid. Chromatography on silica gel (cyclohexane/ethyl acetate 9:1) gives 1.169 g (19%) of yellowish oil which crystallises on standing. MS: m/e=301.3 ($M^++H$).

c) 3-[4-(3-Fluoro-benzyloxy)-phenyl]-but-2-enoic acid methylamide 0.224 g (4 mmol) of KOH is dissolved in 10 ml methanol. 0.4 g (1.33 mmol) of 3-[4-(3-fluoro-benzyloxy)-phenyl]-but-2-enoic acid methyl ester is added and the resulting solution refluxed for 6 hours, concentrated and acidified with 2N aqueous hydrochloric acid. Extraction with ethyl acetate gives 325 mg (85%) of the crude acid. This acid is dissolved in 10 ml of dichloromethane, 2 drops of N,N-dimethylformamide are added and the mixture is cooled to 0° C. Slow addition of 0.380 g (3 mmol) of oxalylchloride yields a yellow solution which is stirred for additional 1.5 hours at RT. Evaporation of the reaction mixture leaves a yellowish resin which is dissolved in 5 ml THF and slowly added at 0° C. to a mixture of 5 ml THF and 5 ml aqueous methylamine (40%). The resulting slurry is stirred at RT for 1 hour, evaporated, diluted with water and extracted three times with ethyl acetate. Chromatography on silica gel (cyclohexane/ethyl acetate 1:1) gives 220 mg (50%) of a colorless solid. MS: m/e=300.2 ($M^++H$).

EXAMPLE 18

3-[4-(3-Fluoro-benzyloxy)-phenyl]-N-methyl-butyramide 100 mg (0.33 mmol) of 3-[4-(3-fluoro-benzyloxy)-phenyl]-but-2-enoic acid methylamide is dissolved in 7 ml methanol. 25 mg of platinum 5% on charcoal is added and the mixture is hydrogenated at RT and normal pressure. The catalyst is filtered off and the filtrate evaporated to dryness, leaving 81 mg of a colorless solid. MS: m/e=302.3 ($M^++H$).

The following Examples A to D are prophetic.

EXAMPLE A

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

An injection solution may have the following composition and is manufactured in usual manner:

| Active ingredient | 1.0 mg |
|---|---|
| 1 N HCl | 20.0 µl |
| acetic acid | 0.5 mg |
| NaCl | 8.0 mg |
| phenol | 10.0 mg |
| 1 N NaOH | q.s. ad pH 5 |
| $H_2O$ | q.s. ad 1 ml |

What is claimed is:

1. A compound of formula I

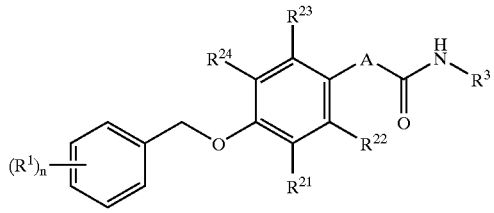

(I)

wherein $R^1$ is $(C_1-C_3)$-alkyl, halogen, halogen-$(C_1-C_6)$-alkyl, cyano, $(C_1-C_6)$-alkoxy or halogen-$(C_1-C_6)$-alkoxy;

$R^{21}$, $R^{22}$, $R^{23}$ and $R^{24}$ are each independently selected from the group consisting of hydrogen and fluoro;

$R^3$ is hydrogen or $(C_1-C_3)$-alkyl;

A is selected from

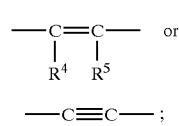

$R^4$ is hydrogen or $(C_1-C_3)$-alkyl;

$R^5$, $R^6$ and $R^7$ are each independently hydrogen or $(C_1-C_6)$-alkyl; and n is 1, 2 or 3;

wherein when n is 2 or 3, each $R^1$ is the same or different; or a pharmaceutically acceptable salt thereof.

2. A compound of according to claim 1, wherein n is 1.

3. A compound according to claim 1, wherein $R^1$ is halogen or halogen-$(C_1-C_6)$-alkyl.

4. A compound according to claim 3, wherein $R^1$ is fluoro or trifluoromethyl.

5. The compound according to claim 1, wherein $R^{21}$, $R^{22}$, $R^{23}$ and $R^{24}$ are hydrogen.

6. A compound according to claim 1, wherein $R^3$ is hydrogen.

7. A compound according to claim 1, wherein $R^3$ is methyl.

8. A compound of formula I-a

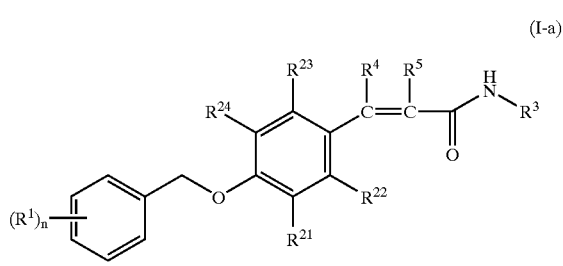

(I-a)

wherein $R^1$ is $(C_1-C_3)$-alkyl, halogen, halogen-$(C_1-C_6)$-alkyl, cyano, $(C_1-C_6)$-alkoxy or halogen-$(C_1-C_6)$-alkoxy;

$R^{21}$, $R^{22}$, $R^{23}$ and $R^{24}$ are each independently selected from the group consisting of hydrogen and fluoro;

$R^3$ is hydrogen or $(C_1-C_3)$-alkyl;

$R^4$ and $R^5$ are each independently hydrogen or $(C_1-C_3)$-alkyl; and n is 1, 2 or 3;

wherein when n is 2 or 3, each $R^1$ is the same or different; or a pharmaceutically acceptable salt thereof.

9. A compound according to claim 8, wherein $R^3$ is methyl.

10. A compound according to claim 9, wherein $R^1$ is fluoro or trifluoromethyl.

11. A compound according to claim 9, wherein $R^1$ is $(C_1-C_3)$-alkyl or $(C_1-C_6)$-alkoxy.

12. A compound selected from the group consisting of
N-methyl-3-[4-(4-methyl-benzyloxy)-phenyl]-acrylamide and
3-[4-(3-methoxy-benzyloxy)-phenyl]-N-methyl-acrylamide.

13. A compound selected from the group consisting of
3-[4-(3-fluoro-benzyloxy)-phenyl]-2,N-dimethyl-acrylamide,
3-[4-(3-fluoro-benzyloxy)-phenyl]-N-methyl-acrylamide,
N-methyl-3-[4-(4-trifluoromethyl-benzyloxy)-phenyl]-acrylamide,
3-[4-(3,4-difluoro-benzyloxy)-phenyl]-N-methyl-acrylamide, and
3-[4-(4-fluoro-benzyloxy)-phenyl]-N-methyl-acrylamide.

14. A compound selected from the group consisting of
3-[4-(3-fluoro-benzyloxy)-phenyl]-2,N-dimethyl-propionamide,
3-[4-(3,4-difluoro-benzyloxy)-phenyl]-propionamide, and
3-[4-(3-fluoro-benzyloxy)-phenyl]-N-methyl-butyramide.

15. A compound of formula I-c

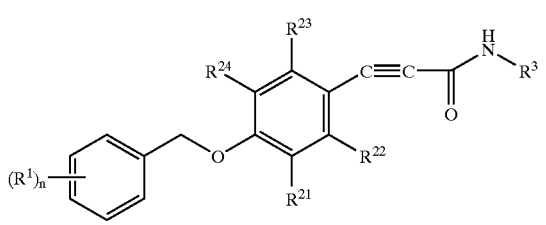
(I-c)

wherein

R$^1$ is (C$_1$–C$_3$)-alkyl, halogen, halogen-(C$_1$–C$_6$)-alkyl, cyano, (C$_1$–C$_6$)-alkoxy or halogen-(C$_1$–C$_6$)-alkoxy;

R$^{21}$, R$^{22}$, R$^{23}$ and R$^{24}$ are each independently selected from the group consisting of hydrogen and fluoro;

R$^3$ is hydrogen or (C$_1$–C$_3$)-alkyl; and n is 1, 2 or 3;

wherein when n is 2 or 3, each R$^1$ is the same or different;

or a pharmaceutically acceptable salt thereof.

16. The compound 3-[4-(3-fluoro-benzyloxy)-phenyl]-propynoic acid methylamide.

17. A composition comprising a compound of formula I

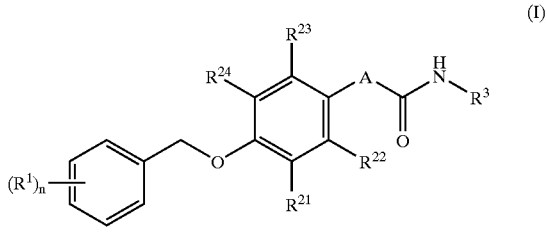
(I)

wherein

R$^1$ is (C$_1$–C$_3$)-alkyl, halogen, halogen-(C$_1$–C$_6$)-alkyl, cyano, (C$_1$–C$_6$)-alkoxy or halogen-(C$_1$–C$_6$)-alkoxy;

R$^{21}$, R$^{22}$, R$^{23}$ and R$^{24}$ are each independently selected from the group consisting of hydrogen and fluoro;

R$^3$ is hydrogen or (C$_1$–C$_3$)-alkyl;

A is selected from

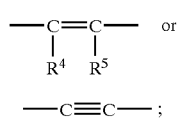

(a)

(b)

R$^4$ is hydrogen or (C$_1$–C$_3$)-alkyl;

R$^5$, R$^6$ and R$^7$ are each independently hydrogen or (C$_1$–C$_6$)-alkyl; and n is 1, 2 or 3; wherein when n is 2 or 3, each R$^1$ is the same or different;

or a pharmaceutically acceptable salt thereof, and a pharmaceutically acceptable carrier.

18. A composition according to claim 17, wherein the compound of formula I is a compound of formula I-a

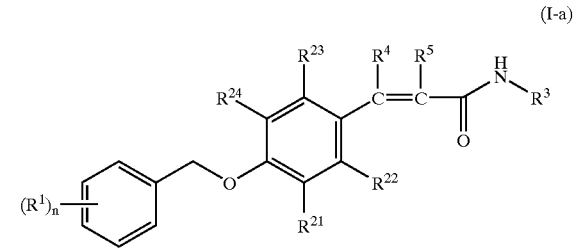
(I-a)

wherein

R$^1$ is (C$_1$–C$_3$)-alkyl, halogen, halogen-(C$_1$–C$_6$)-alkyl, cyano, (C$_1$–C$_6$)-alkoxy or halogen-(C$_1$–C$_6$)-alkoxy;

R$^{21}$, R$^{22}$, R$^{23}$ and R$^{24}$ are each independently selected from the group consisting of hydrogen and fluoro;

R$^3$ is hydrogen or (C$_1$–C$_3$)-alkyl;

R$^4$ and R$^5$ are each independently hydrogen or (C$_1$–C$_3$)-alkyl; and n is 1, 2 or 3;

wherein when n is 2 or 3, each R$^1$ is the same or different;

or a pharmaceutically acceptable salt thereof.

19. A composition according to claim 17, wherein the compound of formula I is a compound of formula I-c

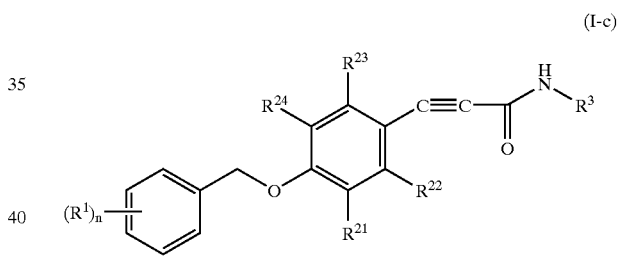
(I-c)

wherein

R$^1$ is (C$_1$–C$_3$)-alkyl, halogen, halogen-(C$_1$–C$_6$)-alkyl, cyano, (C$_1$–C$_6$)-alkoxy or halogen-(C$_1$–C$_6$)-alkoxy;

R$^{21}$, R$^{22}$, R$^{23}$ and R$^{24}$ are each independently selected from the group consisting of hydrogen and fluoro;

R$^3$ is hydrogen or (C$_1$–C$_3$)-alkyl; and n is 1, 2 or 3;

wherein when n is 2 or 3, each R$^1$ is the same or different;

or a pharmaceutically acceptable salt thereof.

20. A process for the manufacture of a compound of formula I according to claim 1, which process comprises a) reacting a compound of formula II

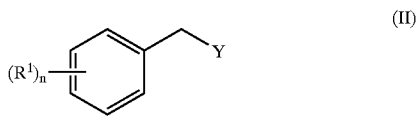
(II)

wherein $R^1$ and n are as defined in claim 1 and Y is a leaving group, with a compound of formula III

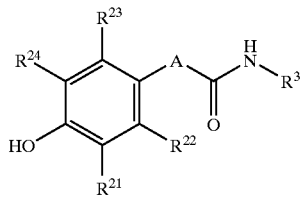

wherein $R^3$, $R^{21}$, $R^{22}$, $R^{23}$, $R^{24}$ and A are as defined in claim 1.

21. A process for the manufacture of a compound of formula I according to claim 1, which process comprises reacting a compound of formula IV

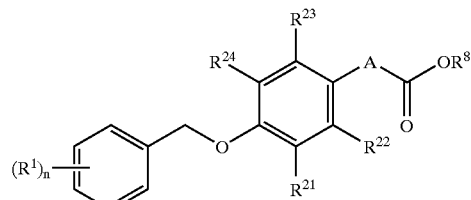

wherein $R^1$, $R^{21}$, $R^{22}$, $R^{23}$, $R^{24}$ and n are as defined in claim 1 and $R^8$ is hydrogen or $(C_1$–$C_6)$-alkyl, with an amine of formula V $$H_2NR^3 \qquad (V)$$

wherein $R^3$ is as defined in claim 1.

* * * * *

UNITED STATES PATENT AND TRADEMARK OFFICE
CERTIFICATE OF CORRECTION

PATENT NO. : 6,900,354 B2
DATED : May 31, 2005
INVENTOR(S) : Jolidon et al.

It is certified that error appears in the above-identified patent and that said Letters Patent is hereby corrected as shown below:

Title page,
Item [73], Assignee, reads "Hoffman-La Roche Inc., Nutley, NJ (US)" should read -- Hoffmann-La Roche Inc., Nutley, NJ (US) --.

Signed and Sealed this

Fourth Day of October, 2005

JON W. DUDAS
*Director of the United States Patent and Trademark Office*